United States Patent
Bock et al.

(10) Patent No.: US 6,893,584 B2
(45) Date of Patent: May 17, 2005

(54) STABILIZED ORGANIC PEROXIDE COMPOSITION AND PROCESS FOR MAKING THE SAME

(75) Inventors: Lawrence A. Bock, Longview, TX (US); Jeff Diffie, Jefferson, TX (US); Peter Frenkel, Longview, TX (US)

(73) Assignee: Crompton Corporation, Middlebury, CT (US)

( * ) Notice: Subject to any disclaimer, the term of this patent is extended or adjusted under 35 U.S.C. 154(b) by 90 days.

(21) Appl. No.: 10/423,165

(22) Filed: Apr. 25, 2003

(65) Prior Publication Data

US 2004/0211938 A1 Oct. 28, 2004

(51) Int. Cl.$^7$ .................. C01B 15/10; A62D 409/34
(52) U.S. Cl. ...................... 252/186.26; 252/186.42; 252/182.29; 252/182.18
(58) Field of Search ............... 252/186.26, 186.42, 252/182.29, 182.18

(56) References Cited

U.S. PATENT DOCUMENTS

| | | | |
|---|---|---|---|
| 3,558,566 A | * | 1/1971 | Balwe et al. ............... 526/321 |
| 3,560,462 A | * | 2/1971 | Farber et al. ............... 526/345 |
| 4,269,726 A | | 5/1981 | Kolczynski et al. |
| 4,396,527 A | | 8/1983 | Matsuyama et al. |
| 4,415,716 A | * | 11/1983 | Lundin et al. ............... 526/209 |
| 4,515,929 A | | 5/1985 | Tang |
| 4,552,682 A | | 11/1985 | Black et al. |
| 4,719,270 A | | 1/1988 | Miwa et al. |
| 4,808,442 A | | 2/1989 | Verlaan et al. |
| 4,952,428 A | | 8/1990 | Keogh |
| 5,104,920 A | | 4/1992 | Keogh |
| 5,110,495 A | | 5/1992 | Self |
| 5,155,192 A | | 10/1992 | Boelema et al. |
| 5,238,978 A | | 8/1993 | Stein |
| 5,541,151 A | | 7/1996 | Sanchez |
| 5,548,046 A | | 8/1996 | Sanchez |
| 5,654,463 A | | 8/1997 | Abma et al. |
| 5,654,464 A | | 8/1997 | Abma et al. |
| 5,714,626 A | | 2/1998 | Abma et al. |
| 5,719,304 A | | 2/1998 | Frenkel et al. |
| 5,892,090 A | | 4/1999 | Frenkel |
| 6,136,926 A | | 10/2000 | Raetzsch et al. |
| 6,153,786 A | | 11/2000 | Henkelmann et al. |
| 6,258,905 B1 | | 7/2001 | Wu et al. |
| 6,399,728 B1 | * | 6/2002 | Stainbrook et al. ...... 526/230.5 |
| 6,437,065 B1 | | 8/2002 | Ritter et al. |
| 2002/0091214 A1 | | 7/2002 | Waanders et al. |
| 2002/0177678 A1 | * | 11/2002 | Stainbrook et al. ...... 526/230.5 |

FOREIGN PATENT DOCUMENTS

| | | |
|---|---|---|
| GB | 2007642 | 11/1978 |
| WO | WO02051879 | 12/2001 |
| WO | WO03/002527 A1 | 1/2003 |

OTHER PUBLICATIONS

English Translation of International Publication No. WO 03/002527 Published in German (Dec., 2001).
Strain, F. et al., "Esters of Peroxycarbonic Acids", J. Am. Chem. Soc. 1950, vol. 72, pp. 1254–1263.

* cited by examiner

Primary Examiner—Joseph D. Anthony
(74) Attorney, Agent, or Firm—Michael P. Dilworth

(57) ABSTRACT

An organic peroxide stabilizing composition comprises an organic peroxide and an organic peroxide stabilizing compound selected from one of the following general formulas (I) or (II):

$$R^1CH\!=\!CH(CH_2)_m(CH\!=\!CH)_n(CH_2)_oR^2 \qquad (I)$$

$$R^4C\!\equiv\!C\!-\!C(O)OR^5 \qquad (II)$$

or mixture thereof wherein $R^1$ is hydrogen, alkyl of from 1 to about 10 carbon atoms, or aryl of from 6 to about 12 carbon atoms, optionally substituted with at least one halogen, lower alkyl, or hydroxy group; $R^2$ is hydrogen, —OH, —C(O)$R^3$ or —C(O)O$R^3$ in which $R^3$ is hydrogen or lower alkyl; $R^4$ and $R^5$ each independently has one of the meanings of $R^1$ and, additionally, $R^4$ can be —C(O)O$R^3$; wherein $R^3$ has one of the same meanings as above and m is 0 or an integer of from 1 to about 20, n is 0 or 1 and o is 0 or an integer of from 1 to about 20 in an amount sufficient to retard the rate of decomposition of the organic peroxide.

12 Claims, No Drawings

STABILIZED ORGANIC PEROXIDE COMPOSITION AND PROCESS FOR MAKING THE SAME

BACKGROUND OF THE INVENTION

1. Field of the Invention

This invention relates to a stabilized organic peroxide composition and process for making the same which comprises an organic peroxide and a stabilizing compound which retards the rate of decomposition of the peroxide compound.

2. Description of the Related Art

Organic peroxides are utilized in a wide variety of chemical applications, including their use as free-radical initiators in the polymerization or copolymerization of ethylenically unsaturated monomers. Organic peroxides are by their very nature unstable and tend to decompose when exposed to elevated temperature or extended storage conditions resulting in liberation of heat and oxygen, putting them at greatly increased risk for fire and/or explosion. As a result, many peroxides must be refrigerated. A variety of stabilizers have been used to stabilize organic peroxides such as peroxydicarbonates. However, there continues to be a need for new and effective stabilizer compositions which can mitigate the hazardous nature of organic peroxides while not interfering with their subsequent use as free-radical initiators.

The use of stabilizers for organic peroxides has been widely known in the art. For example, U.S. Pat. No. 4,515,929 discloses aqueous dispersions of organic peroxides including peroxydicarbonates, which are stabilized against decomposition by the addition of diphenyl peroxydicarbonate or di(alkyl substituted) phenyl peroxydicarbonates.

U.S. Pat. No. 4,552,682 discloses the use of phenolic antioxidants to retard the rate of degradation of aqueous organic peroxide dispersions. The use of phenolic antioxidants is undesirable because they result in discoloration.

U.S. Pat. No. 5,155,192 discloses the use of organic hydroperoxides, e.g., tert-butyl hydroperoxide, to retard the rate of decomposition of peroxydicarbonates.

U.S. Pat. Nos. 5,541,151 and 5,548,046 report thermally stabilized compositions of a dialkyl peroxydicarbonate and a stabilizing amount of an ethylenically unsaturated nitrile or ethylenically unsaturated acetylenic compound.

U.S. Pat. No. 5,654,463 reports the use of alpha-hydroxyalkyl peroxides as stabilizing agents for peroxides, such as peroxydicarbonates.

U.S. Pat. No. 5,654,464 reports the use of cyclic alpha-diketone compounds to retard the rate of decomposition of organic peroxides, such as peroxydicarbonates.

U.S. Pat. No. 5,719,304 reports the use of phosphomolybdic acid as a stabilizing agent for organic peroxides.

U.S. Pat. No. 5,714,626 reports the use of beta-dicarbonyl compounds as stabilizing agents for organic peroxides.

U.S. Pat. No. 5,892,090 reports the use of oximes as materials which will retard the rate of decomposition of organic peroxides.

U.S. Pat. No. 6,399,728 and U.S. Patent Application No. 2002/0177678 report the use of dialkyl maleate and fumarate esters as stabilizing agents for dialkyl peroxydicarbonates. The esters of this invention are incorporated into the polymer during the polymerization process.

U.S. Patent Application No. 2002/0091214 reports the use of reactive phlegmatizers as diluents for organic peroxides. These mixtures are reported to be safe to produce, handle and transport. The phlegmatizers reported include (cyclic) olefins, aldehydes, ketones, alcohols, and mixtures thereof. In particular, olefins such as 1-octene and alpha-methyl styrene are claimed. Many different classes of peroxides are included within the scope of this application. The mixtures of this invention are useful for the polymerization of ethylene, styrene, vinyl chloride, etc. The reactive phlegmatizers are said to be incorporated into the polymer formed during the polymerization process, although no experimental data is given to support this claim.

World Patent Application WO 02/051879 reports reactive diluents for peroxides. In particular, vinyl ethers, such as hydroxybutyl vinyl ether, or a resinous compound containing vinyl ether groups, are reported. The peroxides mentioned in this application include methyl ethyl ketone peroxide, benzoyl peroxide, acetylacetone peroxide and cyclohexanone peroxide. The mixtures are used to cure polyester resins.

World Patent Application WO 03/002527 reports the stabilization of peroxydicarbonates using alpha-unsaturated ketones.

The Journal of The American Chemical Society, Volume 72 pages 1254 to 1263 (1950) discloses the use of, for example, ethyl acetoacetate, iodine, trinitrobenzene, acetanilide, nitromethane, phenol, hydrogen peroxide, and tetralin to retard the rate of decomposition of diisopropyl peroxydicarbonate.

SUMMARY OF THE INVENTION

It is an object of the present invention to provide a stabilized organic peroxide composition.

It is a particular object of the present invention to provide a stabilized peroxydicarbonate composition.

It is a further object of the present invention to provide a stabilized peroxydicarbonate composition which will not impair the use of said peroxydicarbonate as a free-radical initiator in the polymerization or co-polymerization of ethylenically unsaturated monomers.

In keeping with these and other objects of the invention, there is provided a composition comprising an organic peroxide and a stabilizing amount of at least one stabilizing compound of the general formula (I):

$$R^1CH\!=\!CH(CH_2)_m(CH\!=\!CH)_n(CH_2)_oR^2 \qquad (I)$$

or at least one stabilizing compound of the general formula (II):

$$R^4C\!=\!C\!-\!C(O)OR^5 \qquad (II)$$

or mixture thereof, wherein $R^1$ is hydrogen, alkyl of from 1 to about 10 carbon atoms, or aryl of from 6 to about 12 carbon atoms, optionally substituted with at least one halogen, lower alkyl, or hydroxy group; $R^2$ is hydrogen, —OH, —C(O)$R^3$ or —C(O)O$R^3$ in which $R^3$ is hydrogen or lower alkyl; $R^4$ and $R^5$ each independently has one of the meanings of $R^3$ and, additionally, $R^4$ can be —C(O)O$R^3$; wherein $R^3$ has one of the same meanings as above and in is 0 or an integer of from 1 to about 20, n is 0 or 1 and o is 0 or an integer of from 1 to about 20.

DESCRIPTION OF THE PREFERRED EMBODIMENTS

The present invention utilizes various stabilizing compounds which are effective in retarding the rate of decomposition of organic peroxides. Organic peroxides which can be stabilized in accordance with the present invention include peroxydicarbonates of the general formula (III):

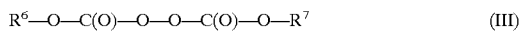
$$R^6-O-C(O)-O-O-C(O)-O-R^7 \quad (III)$$

wherein $R^6$ and $R^7$ each independently is a branched, unbranched, substituted, or unsubstituted alkyl, alkenyl, cycloalkyl, or aromatic group containing up to about 30 carbon atoms and preferably up to about 10 carbon atoms, and the substitution, where present, is one of halogen, nitro, lower alkoxys, aryloxy, acyl, and the like. Some examples of $R^6$ and $R^7$ groups that can be present include, for example, phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

The peroxydicarbonates utilized in this invention can be symmetrical or unsymmetrical, i.e., the $R^6$ and $R^7$ groups can be the same or different. Thus, the peroxydicarbonate can be a mixture containing symmetric peroxydicarbonates, asymmetric peroxydicarbonates or a mixture of symmetric and asymmetric peroxydicarbonates. The peroxydicarbonates utilized in the present invention are preferably those which are a liquid at 0° C. and more preferably a liquid at −5° C. and most preferably a liquid at −25° C.

Specific examples of organic peroxides which can be utilized in the present invention include the aforesaid peroxydicarbonates (III), for example, diethyl peroxydicarbonate, di-n-butyl peroxydicarbonate, diisobutyl peroxydicarbonate and di-4-tert-butylcyclohexyl peroxydicarbonate. Preferable peroxydicarbonates include, for example, di-sec-butyl peroxydicarbonate, di-2-ethylhexyl peroxydicarbonate, di-n-propyl peroxydicarbonate and diisopropyl peroxydicarbonate and the like, and mixtures thereof.

In the structure of stabilizer compound (I), $R^1$ can be hydrogen, an alkyl of from 1 to about 10 carbon atoms, such as methyl, ethyl, propyl, isopropyl, butyl, sec-butyl, tert-butyl, pentyl, hexyl, octyl, and the like, an aryl or substituted aryl of from 6 to about 12 carbon atoms, optionally substituted with at least one halogen, lower alkyl, or hydroxy group, such as methyl, ethyl, propyl, butyl, phenyl, toluyl, xylyl, diphenyl, chlorophenyl, dichlorophenyl, and the like; $R^2$ is hydrogen, —OH, —C(O)$R^3$ or —C(O)O $R^3$ in which $R^3$ is hydrogen or a lower alkyl such as methyl, ethyl, propyl, butyl, and the like; m is 0 or an integer of from 1 to about 20 and is preferably 0 or an integer from 1 to about 7, n is 0 or 1 and o is 0 or an integer of from 1 to about 20 and is preferably 0 or an integer of from 1 to about 8.

Specific stabilizer compounds of formula (I) include, for example methyl crotonate, methyl oleate, oleic acid, 1-octadecene, oleyl alcohol, methyl cinnamate, linoleic acid, methyl linoleate, cinnamyl alcohol, cinnamaldehyde, 4-phenyl-3-buten-2-one, methyl vinyl ketone and mixtures thereof.

In the structure of stabilizer compound (II), $R^4$ and $R^5$ each independently can have one of the meanings of $R^1$ of stabilizer compound (I). Thus, $R^4$ and $R^5$ each independently can be hydrogen, an alkyl of from 1 to about 10 carbon atoms, such as methyl, ethyl, propyl, isopropyl, butyl, sec-butyl, tert-butyl, pentyl, hexyl, octyl, and the like, an aryl or substituted aryl of from 6 to about 12 carbon atoms, optionally, substituted with at least one halogen, lower alkyl, or hydroxy group such as, methyl, ethyl, propyl, isopropyl, butyl, phenyl, toluyl, xylyl, diphenyl, chlorophenyl, dichlorophenyl, and the like. Additionally, $R^4$ can be —(O)O $R^3$ in which $R^3$ has one of the same meanings as $R^3$ of stabilizer compound (I), e.g., hydrogen or lower alkyl such as methyl, ethyl, propyl, butyl, and the like.

Specific stabilizer compounds of formula (II) include propynoic acid, methyl propynoate, ethyl propynoate, propyl propynoate, butyl propynoate, 2-butynoic acid, methyl-2-butynoate, propyl 2-butynoate, butyl 2-butynoate, pentyl 2-butynoate, hexyl 2-butynoate, octyl 2-butynoate, 2-pentynoic acid, ethyl 2-pentynoate, 2-hexynoic acid, methyl 2-hexynoate, 2-heptynoic acid, methyl 2-heptynoate, ethyl 2-heptynoate, methyl 2-octynoate, ethyl 2-octynoate, n-butyl heptynoate, n-butyl phenylpropynoate, methyl 3-phenylpropynoate, and the like, and mixtures thereof.

The stabilizing compound selected will vary in amount based upon the organic peroxide which is being stabilized and conditions such as temperature and intended storage conditions to allow for a broad range of possible quantities based on the said conditions. Generally, the amount of stabilizing compound will be present in an effective organic peroxide stabilizing amount and preferably from about 1% to about 25% by weight of the organic peroxide.

The composition of the present invention displays several significant advantages. Most importantly, as stated above, is greatly improved thermal stability, both in response to exposure to elevating temperature and in response to a given constant temperature. Thermal stability of self-reactive substances such as organic peroxides can be determined by measuring the self-accelerating decomposition temperature (SADT). SADT is recognized as a characteristic for determining the safe storage and transportation of organic peroxides. SADT can be directly correlated with the onset temperature. The onset temperature is the point at which organic peroxides begin uncontrolled thermal decomposition. The onset temperature can be measured by determining the point at which the rate of temperature increase exceeds a certain predetermined value. This is accomplished by gradually increasing the temperature of a sample peroxide enclosed in a sealed cell. The stabilizing compound of the present invention effectively increases the onset temperature of organic peroxides and more particularly, of peroxydicarbonates. As a result, the stabilized peroxydicarbonates of the subject invention have greatly improved thermal properties. In addition, the improved thermal properties do not come at any cost to the effectiveness of the stabilized peroxydicarbonate as a free-radical initiator of polymerization or co-polymerization of ethylenically unsaturated monomers.

The following examples are intended to illustrate the claimed invention and are not in any way designed to limit its scope. Numerous additional embodiments within the scope and spirit of the claimed invention will become apparent to those skilled in the art.

EXAMPLE 1

The onset temperature was measured and compared for samples of pure di-2-ethylhexyl peroxydicarbonate and samples of di-2-ethylhexyl peroxydicarbonate in the presence of each of several different stabilizing compounds. The liquid mixtures were prepared by dissolving the required amount of stabilizer in the peroxydicarbonate.

Using a Differential Thermal Analyzer with an isothermal hold temperature of 30° C. for 15 minutes and then a temperature increase of 1°/minute to 130° C., the onset temperature was measured for a one gram sample of di-2-ethylhexyl peroxydicarbonate in a sealed cell.

The onset temperature was measured by noting the point where the rate of increase (ΔT) of the sample temperature reached 0.2° C./minute. ΔT is the difference between the oven temperature and the sample temperature.

The procedure was repeated with separate samples of the above peroxydicarbonates containing, in turn, the stabilizing compounds listed in Table 1. The results obtained with several examples from the prior art are included for comparison.

The results show that the presence of a stabilizing compound in accordance with the present invention increases the onset temperature at which uncontrolled thermal decomposition of the peroxydicarbonate will begin.

TABLE 1

Onset Temperatures of Decomposition for 98%
Di-(2-ethylhexyl) Peroxydicarbonate with Various Stabilizing Compounds

| Stabilizing Compound | Onset Temp (° C.) By ΔT |
|---|---|
| Comparative Examples | |
| None | 36.8 |
| None (repeat) | 34.9 |
| 25% odorless mineral spirits | 42.4 |
| 1% dibutyl maleate | 43.2 |
| 25% dibutyl maleate | 53.8 |
| 1% dimethyl maleate | 45.4 |
| 25% dimethyl maleate | 52.8 |
| 25% 1-octene | 48.9 |
| 25% cinnamonitrile | 61.7 |
| 25% crotononitrile | 56.5 |
| 25% alpha methyl styrene | 56.3 |
| 1% hydroxybutyl vinyl ether | 33.8 |
| 5% hydroxybutyl vinyl ether | 37.9 |
| Stabilizing Compounds of the Present Invention | |
| 1% methyl crotonate | 42.8 |
| 25% methyl crotonate | 55.1 |
| 1% methyl oleate @70% | 40.4 |
| 25% methyl oleate @70% | 53.6 |
| 1% methyl oleate @99% | 36.3 |
| 25% methyl oleate @99% | 53.0 |
| 1% oleic acid | 40.0 |
| 25% oleic acid | 52.8 |
| 25% 1-octadecene @ 90% | 45.6 |
| 25% oleyl alcohol | 52.3 |
| 25% methyl propiolate | 48.8 |
| 25% methyl cinnamate | 62.7 |
| 25% linoleic acid | 58.0 |
| 25% methyl linoleate | 56.6 |
| 25% cinnamyl alcohol | 56.5 |
| 25% cinnamaldehyde | 56.0 |
| 25% 4-phenyl-3-buten-2-one | 60.7 |
| 10% 4-phenyl-3-buten-2-one | 59.3 |
| 25% methyl vinyl ketone | 53.1 |

EXAMPLE 2

Vinyl chloride was polymerized in a laboratory autoclave using 98.92% di-2-ethylhexyl peroxydicarbonate diluted with 25% by weight of methyl oleate. The polymerization was conducted at 57.2° C. The weight of the initiator used was 0.12% (at 75% active) by weight of the vinyl chloride. The suspending agent, methocel F-50, was used at 0.04% by weight of the vinyl chloride. The conversion of vinyl chloride to PVC was determined to be 50.4% at 150 minutes polymerization time. The percent conversion at 150 minutes was also measured for samples of 98.2% di-2-ethylhexyl peroxydicarbonate diluted with 25% by weight of odorless mineral spirits, 1-octene, or dibutyl maleate. The results, presented in Table 2, show that all four initiator mixtures had the same percent conversion after 150 minutes, within experimental error.

TABLE 2

Polymerization of Vinyl Chloride

| Initiator Diluent | Reference | Vinyl Chloride % Conversion after 150 minutes |
|---|---|---|
| Methyl oleate | Present Invention | 50.4 |
| Odorless Mineral Spirits | Non-Stabilizer | 50.9 |
| 1-octene | U.S. patent application 2002/0091214 | 50.1 |
| Dibutyl maleate | U.S. Pat. No. 6,399,728 | 49.4 |

What is claimed is:

1. A composition comprising an organic peroxide and stabilizing compound of at least one stabilizing compound of the general formula (I):

$$R^1CH=CH(CH_2)_m(CH=CH)_n(CH_2)_oR^2 \quad (I)$$

or at least one stabilizing compound of the general formula (II):

$$R^4C\equiv C-C(O)OR^5 \quad (II)$$

or mixture thereof wherein $R^1$ is hydrogen, alkyl of from 1 to about 10 carbon atoms, or aryl of from 6 to about 12 carbon atoms, optionally substituted with at least one halogen, lower alkyl, or hydroxy group; $R^2$ is —OH; —C(O)$R^3$ or —C(O)O$R^3$ in which $R^3$ is hydrogen or lower alkyl; $R^4$ and $R^5$ each independently has one of the meanings of $R^1$ and, additionally, $R^4$ can be —C(O)O$R^3$; wherein $R^3$ has one of the same meanings as above and m is 0 or an integer of from 1 to about 20, n is 0 or 1 and o is 0 or an integer of from 1 to about 20 in an amount sufficient to retard the rate of decomposition of the organic peroxide.

2. The composition of claim 1, wherein the organic peroxide is of the general formula (III):

$$R^6-O-C(O)-O-O-C(O)-O-R^7 \quad (III)$$

wherein $R^6$ and $R^7$ each independently is a branched, unbranched, substituted, or unsubstituted alkyl, alkenyl, cycloalkyl, or aromatic group containing up to about 30 carbon atoms.

3. The composition of claim 2, wherein each $R^6$ and $R^7$ is independently an alkyl, or aromatic group containing up to about 10 carbon atoms.

4. The composition of claim 3, wherein each $R^6$ and $R^7$ is independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl, 2-nitro-2-methylpropyl and mixtures thereof.

5. The composition of claim 2, wherein the organic peroxide is a peroxydicarbonate.

6. The composition of claim 5, wherein the peroxydicarbonate is selected from the group consisting of diethyl peroxydicarbonate, di-n-butyl peroxydicarbonate, diisobutyl peroxydicarbonate, di-4-tert-butylcyclohexyl peroxydicarbonate, di-sec-butyl-peroxydicarbonate, di-2-ethylhexyl peroxydicarbonate, di-n-propyl peroxydicarbonate, diisopropyl peroxydicarbonate, and mixtures thereof.

7. The composition of claim 5, wherein the peroxydicarbonate is a liquid at 0° C.

8. The composition of claim 5, wherein the peroxydicarbonate is a liquid at −5° C.

9. The composition of claim 5, wherein the peroxydicarbonate is a liquid at −25° C.

10. The composition of claim 1, wherein the stabilizing compound (I) is selected from the group consisting of methyl crotonate, methyl oleate, oleic acid, oleyl alcohol, methyl cinnamate, linoleic acid, methyl linoleate, cinnamyl alcohol, cinnamaldehyde, 4-phenyl-3-buten-2-one, methyl vinyl ketone and mixtures thereof.

11. The composition of claim 1, wherein the stabilizing compound (II) is selected from the group consisting of include propynoic acid, methyl propynoate, ethyl propynoate, propyl propynoate, butyl propynoate, 2-butynoic acid, methyl-2-butynoate, propyl 2-butynoate, butyl 2-butynoate, pentyl 2-butynoate, hexyl 2-butynoate, octyl 2-butynoate, 2-pentynoic acid, ethyl 2-pentynoate, 2-hexynoic acid, methyl 2-hexynoate, 2-heptynoic acid, methyl 2-heptynoate, ethyl 2-heptynoate, methyl 2-octynoate, ethyl 2-octynoate, n-butyl heptynoate, n-butyl phenylpropynoate, methyl 3-phenylpropynoate and mixtures thereof.

12. The composition of claim 1, wherein the stabilizing compound is present in an amount of from about 0.1% to about 25% by weight of the organic peroxide present.

* * * * *